(12) United States Patent
Fisher

(10) Patent No.: US 11,278,650 B2
(45) Date of Patent: *Mar. 22, 2022

(54) HALTER SUPPORT DEVICE FOR USE WITH LACTATION PUMP COLLECTION CONTAINERS

(71) Applicant: Grace Fisher, Calabasas, CA (US)

(72) Inventor: Grace Fisher, Calabasas, CA (US)

(*) Notice: Subject to any disclaimer, the term of this patent is extended or adjusted under 35 U.S.C. 154(b) by 3 days.

This patent is subject to a terminal disclaimer.

(21) Appl. No.: 16/921,018

(22) Filed: Jul. 6, 2020

(65) Prior Publication Data

US 2020/0330663 A1 Oct. 22, 2020

Related U.S. Application Data

(63) Continuation of application No. 16/195,570, filed on Nov. 19, 2018, now Pat. No. 10,702,639.

(60) Provisional application No. 62/589,784, filed on Nov. 22, 2017.

(51) Int. Cl.
*A41C 3/04* (2006.01)
*A61M 1/06* (2006.01)

(52) U.S. Cl.
CPC .............. *A61M 1/062* (2014.02); *A41C 3/04* (2013.01); *A61M 2209/088* (2013.01)

(58) Field of Classification Search
CPC ... A61M 1/062; A61M 2209/088; A41C 3/04; A45F 5/00; A45F 2003/002
See application file for complete search history.

(56) References Cited

U.S. PATENT DOCUMENTS

| | | |
|---|---|---|
| 4,629,153 A | 12/1986 | Marcum |
| 5,514,166 A | 5/1996 | Silver et al. |
| 5,571,084 A | 11/1996 | Palmer |
| 6,004,186 A | 12/1999 | Penny |
| 6,247,996 B1 | 6/2001 | Fields |
| 6,379,327 B2 | 4/2002 | Lundy |
| 6,524,288 B1 | 2/2003 | Hadley-Fruit |
| 6,764,377 B2 | 7/2004 | Gillan |
| 6,974,361 B2 | 12/2005 | Cravaack et al. |
| 7,611,399 B2 | 11/2009 | Brigham |
| 7,950,980 B2 | 5/2011 | Solberg et al. |
| 8,414,353 B1 | 4/2013 | Leavell |
| 9,498,005 B2 | 11/2016 | Abbaszadeh |
| 2012/0187138 A1 | 7/2012 | Vasquez et al. |
| 2012/0197187 A1 | 8/2012 | LaFave |

*Primary Examiner* — Corey N Skurdal
(74) *Attorney, Agent, or Firm* — Trojan Law Offices

(57) ABSTRACT

A halter support apparatus for carrying milk collection containers comprise a halter strap and at least one support cup. The at least one support cup is capable of carrying the milk collection containers. The halter strap is connected to at least one support cup to support the weight of the milk collection containers. The halter strap is adjustable such that the milk collection containers inside the at least one support cup can be suspended in place near the user's breasts. The halter support apparatus also includes an elastic band wrapped around the user's body for securing the attachment of the breast shields to the user's breasts.

20 Claims, 8 Drawing Sheets

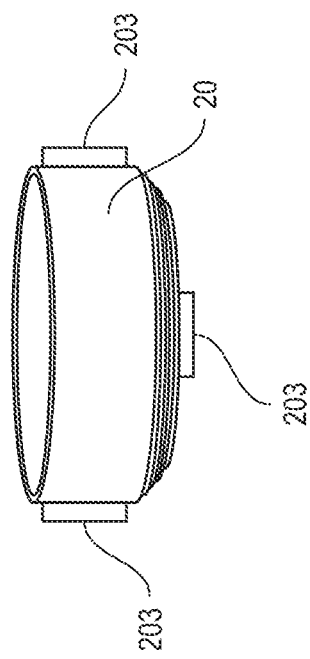
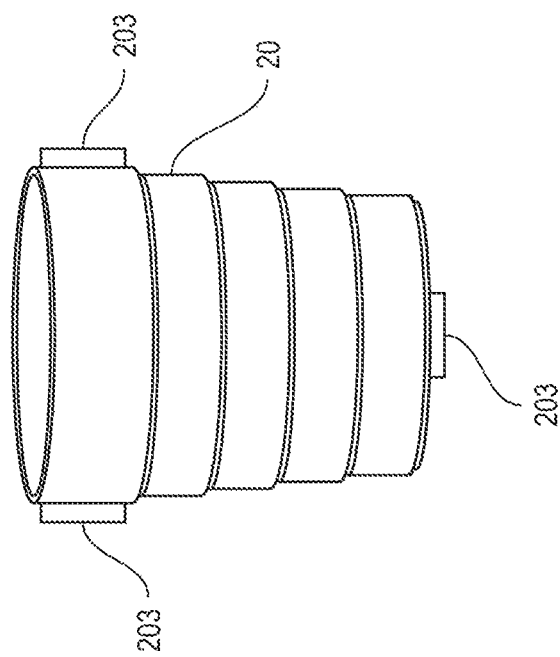

HALTER SUPPORT DEVICE FOR USE WITH LACTATION PUMP COLLECTION CONTAINERS

CROSS-REFERENCE TO RELATED APPLICATIONS

This application is a continuation of application Ser. No. 16/195,570, filed on Nov. 19, 2018, which claims priority from Provisional Application No. 62/589,784, filed on Nov. 22, 2017, the content of which is incorporated by reference in its entirety.

FIELD OF THE INVENTION

The present invention relates to an apparatus for securing and supporting pumping devices that extract milk from lactating women, and more particularly, to a halter apparatus that supports the weight of milk collection containers for breast milk pumping.

BACKGROUND OF THE INVENTION

Traditionally, portable hands-free breast pumping apparatuses enable a lactating woman to collect milk without holding the breast pump in place so as to free the woman to perform other tasks. Apparatuses for pumping breast milk typically include a breast pump for pumping the breast milk, a breast shield which covers and attaches the pump to the breast, suction tubing for connecting the pump to the breast shield, and a bottle, bottles or other collection containers connected to the breast shield for collecting the breast milk. Additionally, a separate support strap or brassiere is required to secure the pump to the breasts by securing the pump's breast shield to the breasts. The support brassieres or straps used in "hand-free" style pumping, normally function by holding the pump's breast shield to breasts.

For examples, the U.S. Pat. No. 6,247,996 issued to Angel Fields (Fields '996 patent), entitled "Breast Milk Pump Support Harness," teaches to secure the breast milk pump against the breast and discloses that "detachable collection bottle support assemblies" are attached to the brassiere at fix locations and not to the halter strap. The attachment of the support cups to the brassier would also create torque on the breasts and nipples due to the increasing weight of the milk collection containers. Thus, the device in the Field '996 would not provide as much support to the milk collection containers from underneath, and would increase the chance of pulling on the breasts and nipples from the weight of the milk collection containers.

Further, the U.S. Pat. No. 6,764,377 issued to Jonathan C. Gillan (Gillan '377 patent), entitled "Hands-Free Breast Milk Expression System," teaches "a strap can suspend from a nursing mother's neck, thereby suspending a pair of breast milk collection devices near the nursing mother's breast." Though the Gillan '377 patent discloses that the strap can secure the milk collection devices in positions near the breasts, it does not teach the support of the weight of the milk collection containers.

Similarly, the U.S. Pat. No. 7,611,399 issued to Merilee Brigham (Brigham '399 patent), entitled "Hands-Free Breast Pumping Support Device," also discloses an adjustable strap, but the strap is connected with the breast pumping device and does not support the weight of the milk collection containers. Neither Gillan '377 patent nor Brigham '399 patent includes support cups to fully secure and support the increasing weight of the milk collection containers.

Since these apparatuses do not support the weight of the milk collection containers from underneath when the milk is being collected, the disadvantage of such apparatuses is that as the volume of milk pumped increase, the weight of the milk in the milk collection containers may pull down on the breasts and nipples, which can cause great discomfort and subsequently cause the mother to have to hold the milk collection containers to support their weight, thus requiring the use of the user's hands. In short, the practical "hands-free" pumping requires utility of two mechanisms: that of securing the breast shield to the breast, and that of supporting the weight of the collection containers from underneath.

The object of the present invention is to provide a convenient hands-free nursing system that can support the weight of the milk collection containers, including bottles, bags, or other receptacles, so as to eliminate any pull on the breasts and use of the user's hands to support the weight of the milk collection containers.

More specifically, the object of the present invention provides a halter support device for carrying and supporting the milk collection containers so that there is no need for the user to hold the milk collection containers during breast pumping, while also preventing the breast shields and the increasing weight of the milk collection containers from pulling down on the breasts and nipples of the user.

SUMMARY OF THE INVENTION

In accordance with the objectives of the invention, the embodiments of the present invention relate to a halter support apparatus for carrying milk collection containers. The halter support apparatus comprises a halter strap, and at least one support cup. The halter strap includes an adjustable neck strap. The at least one support cup is capable of carrying the milk collections containers. The halter strap is connected to the at least one support cup to support the weight of the milk collection containers. The halter strap is adjustable such that the milk collection containers are suspended near the user's breasts.

In one embodiment of the present invention, the halter strap is connected to the at least one support cup by attaching at the sides of the at least one support cup. Particularly, the halter strap can be attached to the at least one support cup by fasteners integrated with the at least one support cup. The halter strap can also be attached to the at least one support cup with brackets.

In one embodiment of the present invention, the at least one cup comprises a pair of support cup; in another embodiment, the halter strap can be configured to connect to only one support cup.

In a preferred embodiment of the present invention, the halter apparatus includes an elastic band wrapped around the user's body for securing the attachment of the breast shields to the user's breasts.

In one embodiment of the halter support apparatus for carrying milk collection containers, there is provided a breast pumping method. The at least one support cup is connected to the flexible halter strap, and the milk collection containers are placed inside the at least one support cup. The flexible halter strap connected to the at least one support cup is placed around the user's neck. In this way, the milk collection containers are suspended near the user's breasts to collect milk therefrom. When the user expresses milk into the milk collection containers, the weight of the milk collection containers is supported by the at least one support cup from underneath.

BRIEF DESCRIPTION OF THE DRAWINGS

FIG. 6A illustrates an embodiment of the support cup in a collapsible design.

FIG. 6B illustrates another embodiment of the support cup in the collapsible design.

FIG. 8 illustrates an embodiment of the elastic band, where the elastic band has slit holes for the breast shields to be inserted through.

DETAILED DESCRIPTION OF EMBODIMENTS

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and to fully convey the scope of the invention to those skilled in the art.

Figure 1:
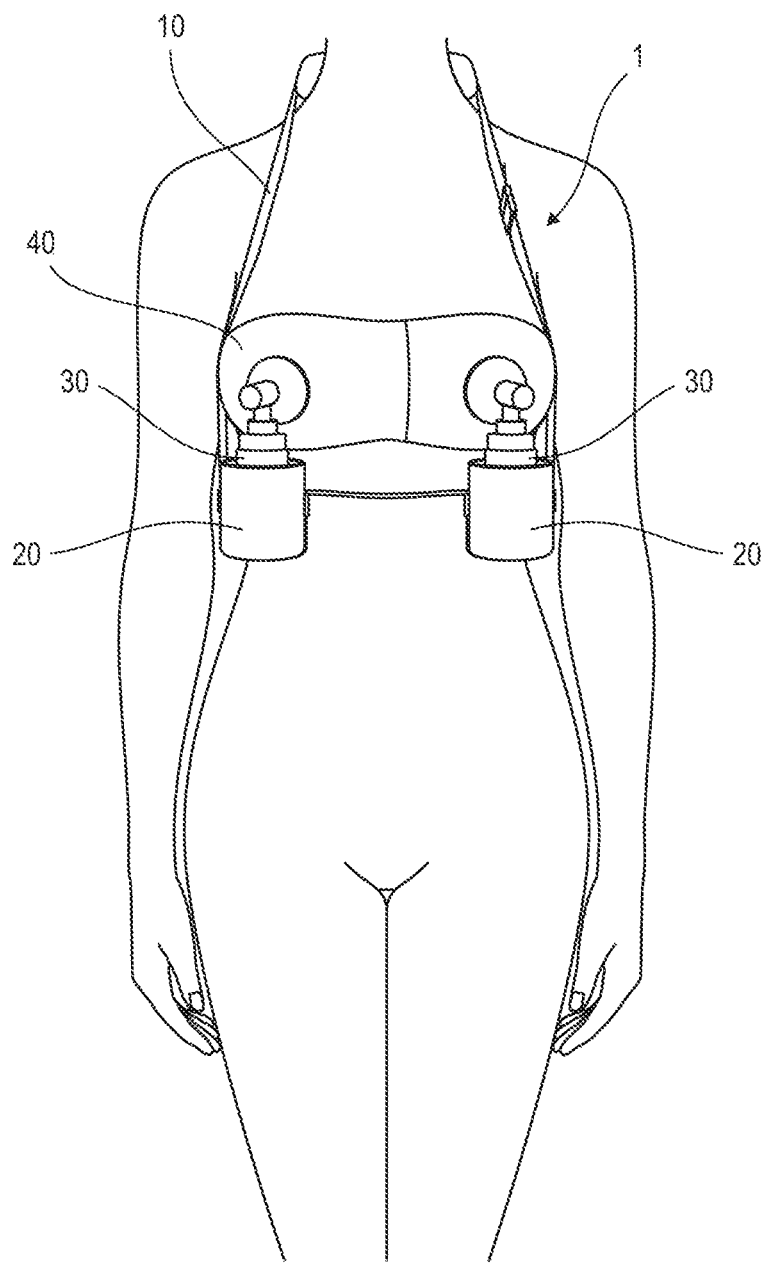
FIG. 1 illustrates a front view of an embodiment of the invention having milk collection containers inside the support cups.
Figure 2A:
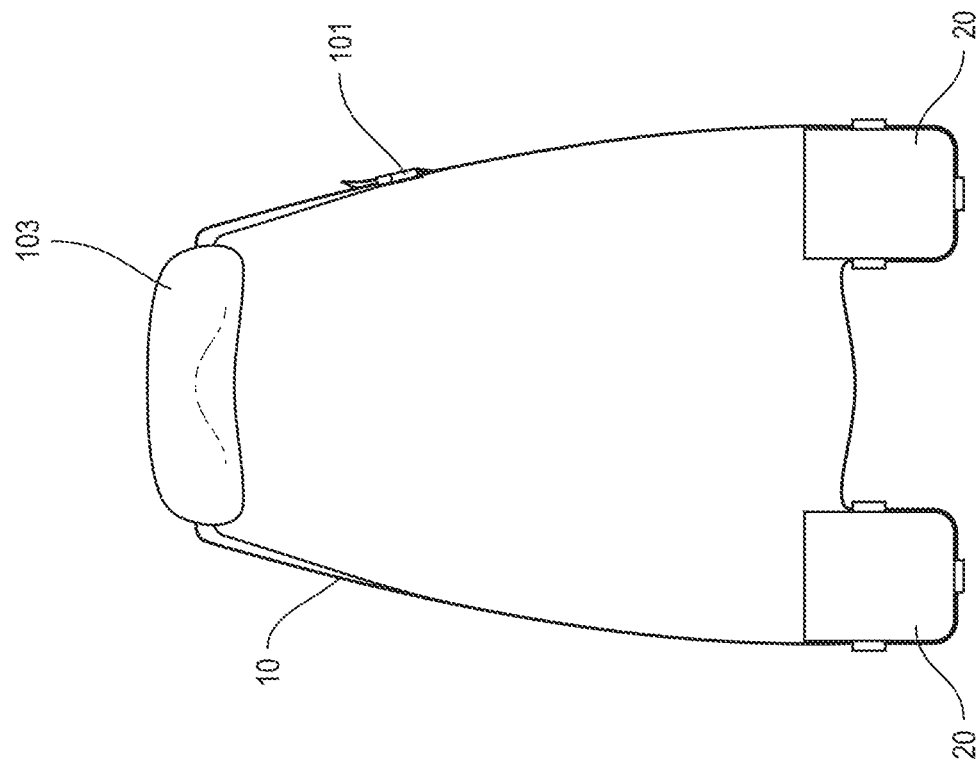
FIG. 2A illustrates an embodiment of the halter strap having an adjustable buckle for adjustment or detachable release.
Figure 2B:
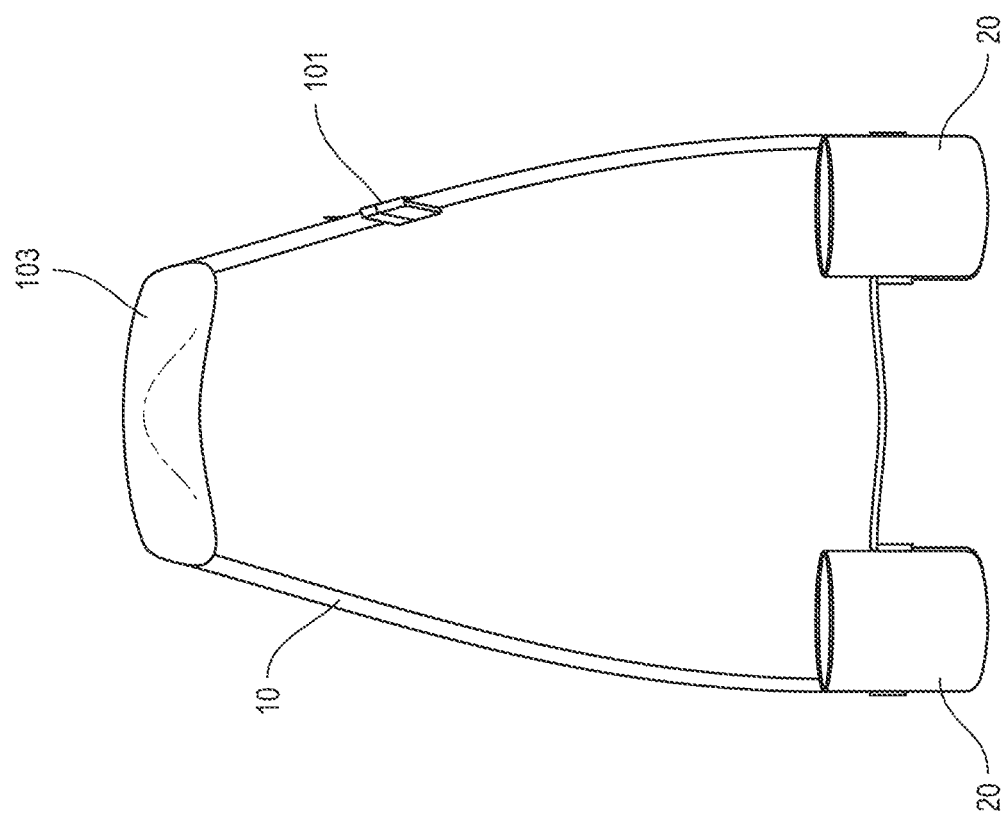
FIG. 2B illustrates an embodiment of the invention having a padded cushion attached to the halter strap.

As shown in FIG. 1, a halter support apparatus 1 according to an embodiment of the invention is comprised of a halter strap 10, and one or more support cups 20. The halter strap 10 is removably connected to the support cups 20, and the milk collection containers 30 are carried by the support cups 20. In one embodiment, the support cups 20 can carry different sizes of the milk collection containers 30. FIG. 1 also shows that the halter strap 10 can be placed over the user's head and around the user's neck. The halter strap 10 is flexible in length, allowing the user to properly place the support cups 20 in front of the user's body near the breasts, as shown in FIG. 1. As further shown in FIG. 2A, the halter strap 10 is adjustable and can be detachable, released via an attached clasp or buckle 101. In one embodiment, the halter strap 10 includes a padded cushion 103 to provide greater comfort around the user's neck as shown in FIG. 2B.

Figure 3C:
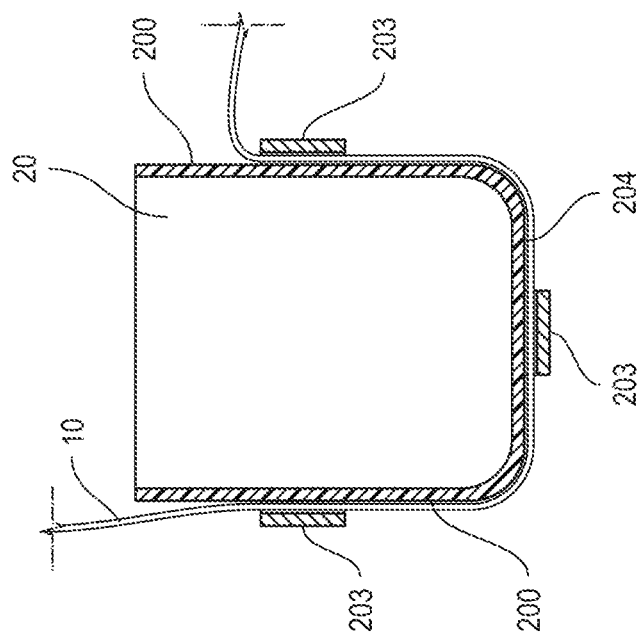
FIG. 3C illustrates a side view of an embodiment of the invention showing the halter strap attached to the support cup with brackets on two sides and from underneath.
Figure 3B:
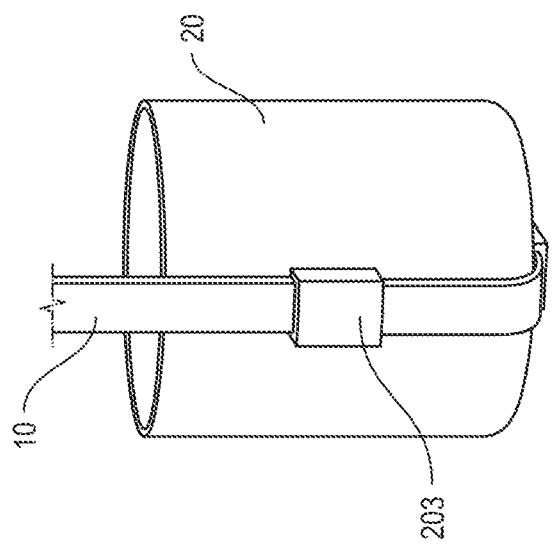
FIG. 3B illustrates an embodiment of the halter strap to be secured to the support cup with brackets.
Figure 3A:
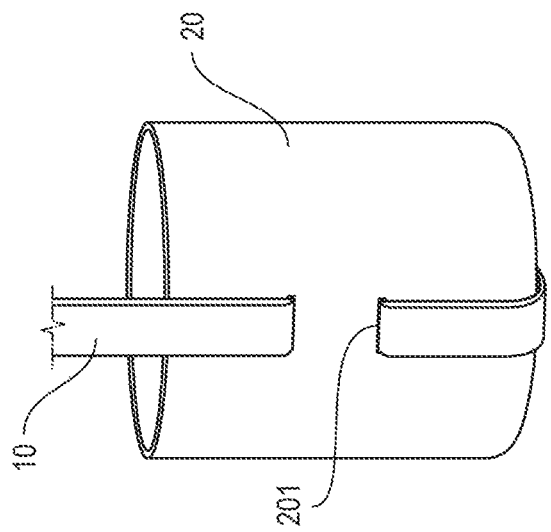
FIG. 3A illustrates an embodiment of the halter strap to be attached to the support cup by fasteners integrated with the cup.

Referring now to FIGS. 3A, 3B, and 3C, the halter strap 10 is removably connected to the support cups 20. In one embodiment, the halter strap 10 of the halter support apparatus 1 connects to the support cups 20 by attaching at the sides of the support cups 20. In one embodiment, the halter strap 10 can be attached to the support cups 20 by fasteners 201 integrated within the support cups 20, as shown in FIG. 3A. In another embodiment, the halter strap 10 can be attached to the support cups 20 with brackets 203, as shown in FIG. 3B. In a preferred embodiment, the halter strap 10 is attached to the support cup 20 with brackets 203 on two sides 200 and also from underneath 204 such that the halter strap 10 is secured to each support cup 20 with enough stability to support the weight of the milk collection containers 30 when the user expresses the milk from the breasts. As best shown in FIG. 3C, the halter strap 10 is connected to two sides 200 of the support cup 20 secured by the brackets 203 and the underneath 204 of the support cup 20 secured by the bracket 203.

Figure 4:
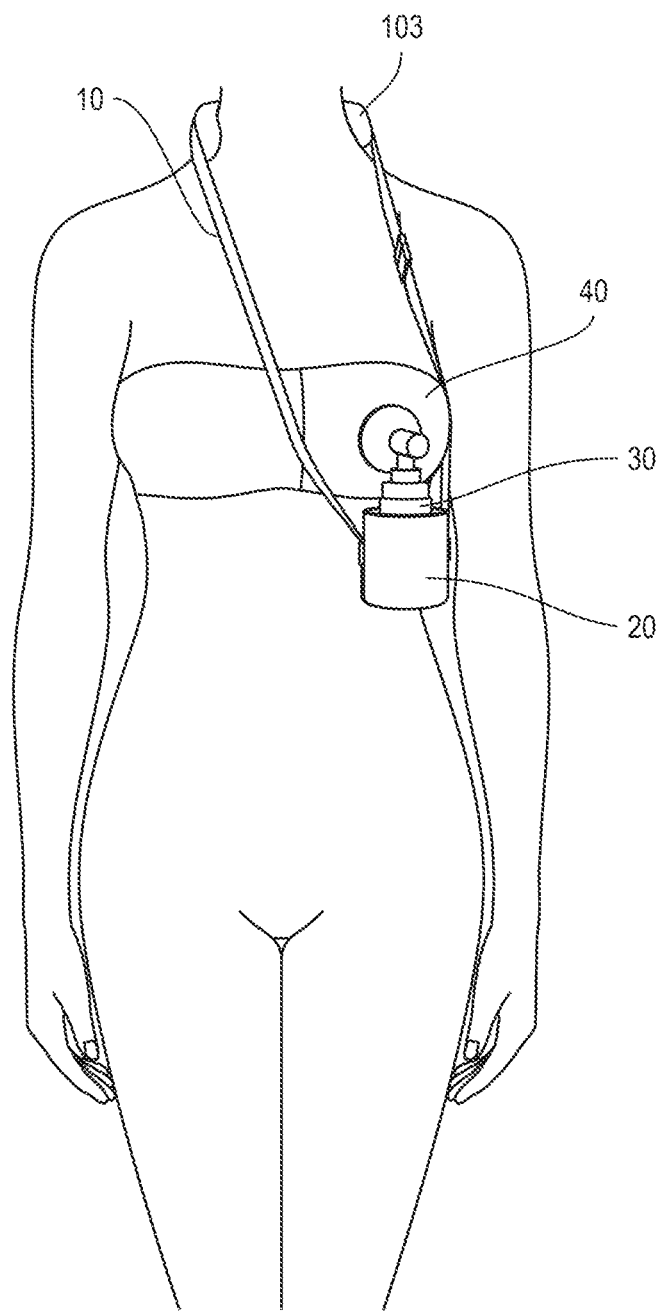
FIG. 4 illustrates a front view of an embodiment of the invention with one support cup connected to the halter strap.

The halter strap 10 of the halter support apparatus 1 can connect to the support cups 20 in a variety of ways. As shown in FIG. 1, the halter strap 10 of the halter support apparatus 1 is connected to a pair of support cups 20 configured to support two milk collection containers 30 that allows the simultaneous pumping of both of the user's breasts while providing balance between the two milk collection containers 30. In another embodiment, the halter support apparatus 1 can also be reconfigured to support only one support cup 20 for pumping from only one of the user's breasts, as shown in FIG. 4. The halter strap 10 is connected to only one support cup 20 to accommodate the user who expresses milk only from one side of the breasts. Since only one support cup 20 is suspended near the user's breast, the user can also pump milk into the milk collection container 30 on one side of the breasts while nursing on the other side.

Figure 5:
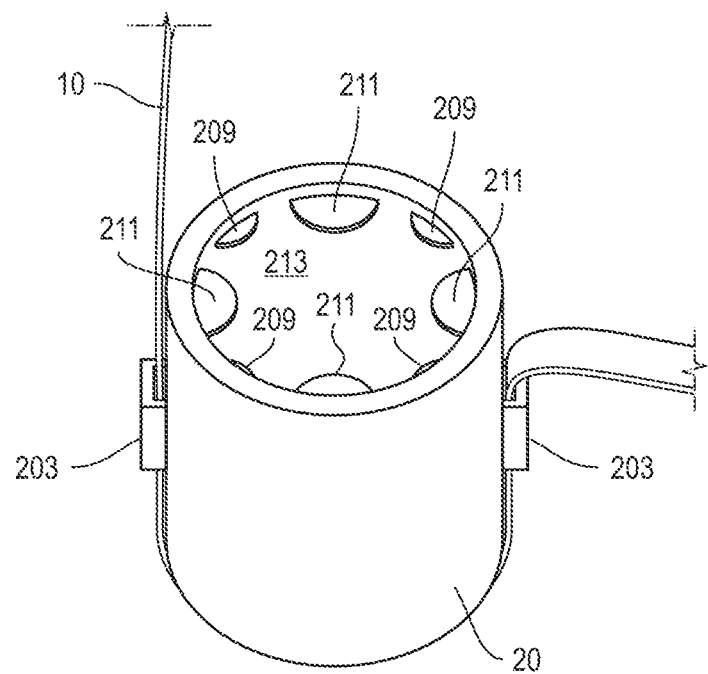
FIG. 5 illustrates an embodiment of the support cup from a top perspective showing flanges inside the support cup.

To secure different sizes of milk collection containers 30 in the support cups 20, the support cups may include one or more flanges 209, 211 inside 213 the support cups 20 as shown in FIG. 5. When the milk collection containers 30 are placed inside 213 the supports cups 20, they can be held securely by the flanges 209, 211 such that the support cups 20 can support the weight of the milk collection containers 30 while collecting the milk from the breasts.

In a preferred embodiment as shown in FIG. 6A, the support cups 20 of the halter support apparatus 1 can be made of collapsible materials such that the support cups 20 are collapsible to lay flat, as shown in FIG. 6B, for easy transport or storage of the halter support apparatus 1.

Figure 7:
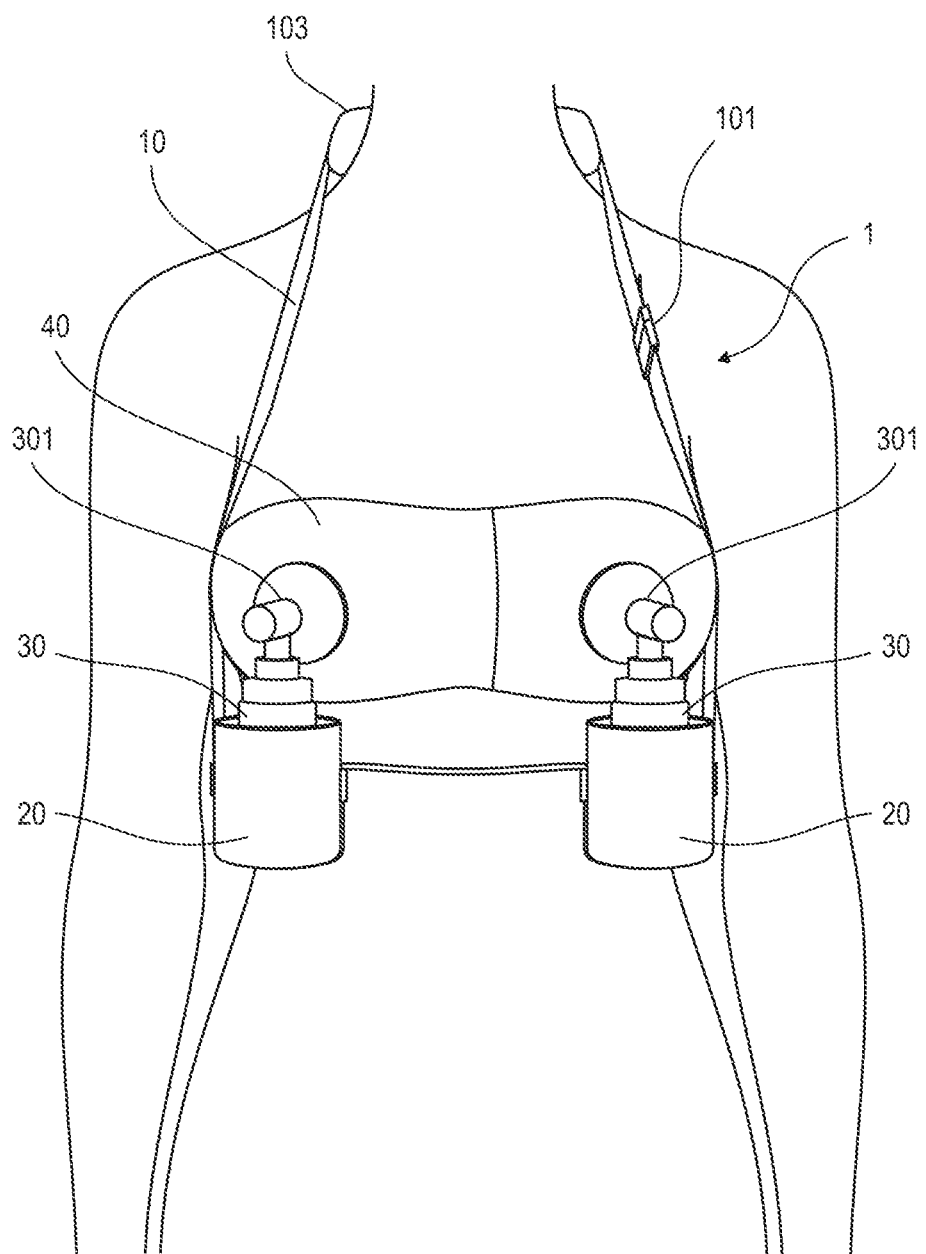
FIG. 7 illustrates a front view of an embodiment of the invention, having an elastic band around the user's body.
Figure 8:
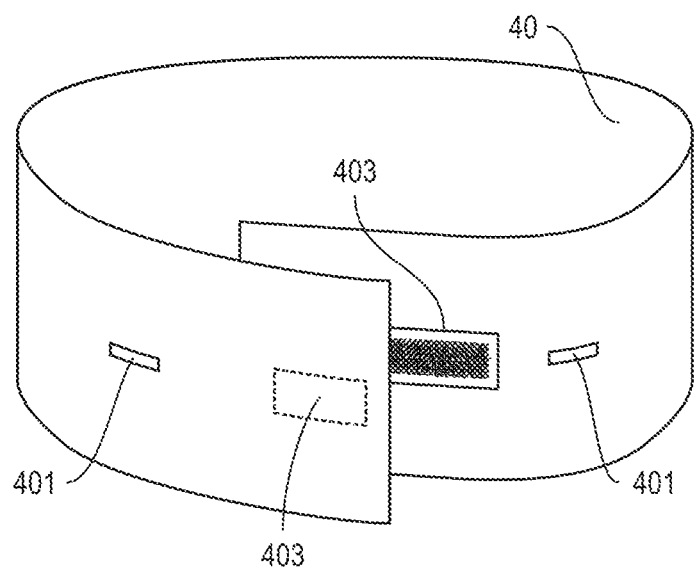

Referring now to FIG. 7, in one embodiment, the halter support apparatus 1 has an elastic band 40 that can be independent from the halter strap 10 and the support cups 20. The elastic band 40 can be adjustably wrapped around the user's body to secure the attachment of the breast shields 301. Particularly, because the milk collection containers 30 are connected to the breast shields 301, the elastic band 40, attached with the breast shields 301, can place the milk collection containers 30 near the user's breasts. In addition, the elastic band 40 can hold the breast shields 301 to the breasts such that it helps creates suction of the breast shields 301 to the user's breasts. Further shown in FIGS. 7 and 8, the elastic band 40 has slit holes 401 for breast shields 301 to be inserted through for collecting milk from the breasts. In this way, the elastic band 40 can hold the breast shields 301 in place, and further protects the milk collection containers' 30 increasing weight from pulling down on the user's breasts and nipples. In one embodiment, the elastic band 40 has the fasteners 403 such as Velcro fasteners inside the band 40 to securely wrap the user's body.

While illustrative embodiments of the invention have been described in detail above, it is to be understood that the appended claims are intended to be construed to include variations of the present invention.

What is claimed is:

1. A halter support apparatus for supporting milk collection containers, comprising:
   a halter strap, said halter strap including an adjustable neck strap;
   at least one support cup, said at least one support cup being capable of supporting at least one of said milk collection containers;
   an elastic band, said elastic band wrapped around a user's body;
   wherein said halter strap is directly connected to said at least one support cup to support the weight of said at least one milk collection containers;
   wherein said elastic band is capable of securing said at least one milk collection containers to said user's breast.

2. A halter support apparatus for supporting milk collection containers of claim 1, wherein said halter strap is adjustable via an attached side buckle.

3. A halter support apparatus for supporting milk collection containers of claim 1, wherein said halter strap is connected to said at least one support cup by attaching at the sides of said at least one support cup.

4. A halter support apparatus for supporting milk collection containers of claim 3, wherein said halter strap is attached to said at least one support cup by fasteners integrated with said at least one support cup.

5. A halter support apparatus for supporting milk collection containers of claim 3, wherein said halter strap is attached to said at least one support cup with brackets.

6. A halter support apparatus for supporting milk collection containers of claim 1, wherein said halter strap is secured underneath said at least one support cup.

7. A halter support apparatus for supporting milk collection containers of claim 1, wherein said at least one support cup further has flanges for holding various sizes of said milk collection containers.

8. A halter support apparatus for supporting milk collection containers of claim 1, wherein said elastic band secures said at least one milk collection containers to said user's breast with a breast shield.

9. A halter support apparatus for supporting milk collection containers of claim 1, wherein said at least one support cup further includes a pair of support cups.

10. A halter support apparatus for supporting milk collection containers of claim 9, wherein said halter strap is configured to connect to one of said pair of support cups.

11. A halter support apparatus for supporting milk collection containers, comprising:
    a halter strap, said halter strap including an adjustable neck strap;
    at least two support cups, said support cups being capable of individually supporting at least one of said milk collection containers;
    a connecting strap directly connecting said support cups;
    wherein said halter strap is directly connected to said at least two support cups to support the weight of said milk collection containers;
    wherein said connecting strap is capable of creating tension between said at least two support cups to stabilize said at least two support cups.

12. A halter support apparatus for supporting milk collection containers of claim 11, wherein said halter strap is adjustable via an attached side buckle.

13. A halter support apparatus for supporting milk collection containers of claim 11, wherein said halter strap is directly connected to said at least two support cups by attaching at the sides of said at least two support cups.

14. A halter support apparatus for supporting milk collection containers of claim 11, wherein said halter strap is directly attached to said at least two support cups by fasteners integrated with said at least two support cups.

15. A halter support apparatus for supporting milk collection containers of claim 11, wherein said halter strap is secured underneath said at least two support cups.

16. A halter support apparatus for supporting milk collection container of claim 11, wherein said halter strap is configured to directly connect to one of said at least two support cups.

17. A halter support apparatus for supporting milk collection containers of claim 11, further comprising an elastic band wrapped around said user's body for securing the attachment of said milk collection containers to said user's breasts.

18. A method for breast milk pumping and supporting milk collection containers, the method comprising:
    directly connecting at least one support cup to a halter strap;
    supporting at least one of said milk collection containers with said at least one support cup;
    placing said halter strap around a user's neck;
    wrapping an elastic band around said user's body;
    securing at least one of said milk collection containers to said user's breast with said elastic band; and
    expressing breast milk from said user's breast into said at least one milk collection containers secured by said elastic band and supported by said at least one support cup.

19. The method of claim 18, said method further comprising:
    directly connecting said halter strap to a pair of support cups;
    supporting a pair of said milk collection containers with said pair of support cups; and
    enabling said user to simultaneously express breast milk from both breasts to said pair of milk collection containers.

20. The method of claim 19, said method further comprising:
    directly connecting said halter strap to one of said pair of support cups such that said user can express milk to one of said pair of milk collection containers from one side while nursing on the opposite side from said user's breast.

* * * * *